United States Patent [19]

Akashi et al.

[11] Patent Number: 5,079,093
[45] Date of Patent: Jan. 7, 1992

[54] EASILY-SLIPPERY MEDICAL MATERIALS AND A METHOD FOR PREPARATION THEREOF

[75] Inventors: Ryojiro Akashi; Shoji Nagaoka, both of Kanagawa, Japan

[73] Assignee: Toray Industries, Inc., Tokyo, Japan

[21] Appl. No.: 465,237

[22] PCT Filed: Aug. 9, 1989

[86] PCT No.: PCT/JP89/00812

§ 371 Date: Jun. 4, 1990

§ 102(e) Date: Jun. 4, 1990

[87] PCT Pub. No.: WO90/01344

PCT Pub. Date: Feb. 22, 1990

[30] Foreign Application Priority Data

Aug. 9, 1988 [JP] Japan .................................. 63-199294
Apr. 17, 1989 [JP] Japan .................................... 1-96952

[51] Int. Cl.⁵ .............................................. B32B 9/04
[52] U.S. Cl. ............................... 428/411.1; 428/424.4; 428/463; 428/483; 428/520; 427/402; 427/407.1

[58] Field of Search ................... 604/265; 428/411.1, 428/424.4, 463, 476.3, 483, 520; 427/299, 402, 407.1

[56] References Cited

U.S. PATENT DOCUMENTS 4,100,309 7/1978 Micklus et al. ........................... 427/
4,729,914 3/1988 Kliment et al. .......................... 428/

FOREIGN PATENT DOCUMENTS

A-0093093 11/1983 European Pat. Off. .
A-0106004 4/1984 European Pat. Off. .
0217771 4/1987 European Pat. Off. .

Primary Examiner—Merrell C. Cashion, Jr.
Assistant Examiner—D. S. Nakarani
Attorney, Agent, or Firm—Nixon & Vanderhye

[57] ABSTRACT

The present invention provides a medical material having an easily-slippery property and durability which the conventional technologies have never provided by fixing a hydrophilic polymer on the surface of a base material through strong covalent bondings and a method for preparation thereof.

20 Claims, No Drawings

EASILY-SLIPPERY MEDICAL MATERIALS AND A METHOD FOR PREPARATION THEREOF

TECHNOLOGICAL FIELD

The present invention relates to a medical material wherein a hydrophilic coating exhibiting excellent low frictional property, namely, easily-slippery property on wetting is formed on the surface of a base material and a method for preparation thereof.

BACKGROUND TECHNOLOGY

For medical materials including physiological and hygienic material etc., especially for catheters and guide wires, low frictional property (easily-slippery property) of the surface is one of the essential requirements. For example, if these materials have no easily-slippery property, when a catheter is inserted in a human body, there is the possibility that a pain could be accompanied with it or a damage or an inflammation of tissue mucosa could occur.

As conventional technologies providing the easily-slippery property, a method wherein the surface of a base material is coated with a variety of oils, a method wherein the surface of the base material is coated with a polymer having a low friction coefficient such as Teflon and a method wherein it is coated with a hydrophilic polymer are in public use. It is understood that especially, coating with a hydrophilic polymer is superior one from the viewpoints of practical use and safety.

As the practical methods for coating with a hydrophilic polymer, fixation of polyvinyl pyrrolidone with an isocyanate (Japanese Patent Laid-Open No.19,582/1984, U.S. Pat. No.4,100,309), a method using a hydrophilic polymer copolymerized with a reactive functional group and an isocyanate (Japanese Patent Laid-Open No.81,341/1984), fixation of polyethylene oxide with an isocyanate (Japanese Patent Laid-Open No.193,766/1983) are disclosed.

However, the method wherein the surface of a base material is coated with a variety of oils exhibits low durability and has a problem of safety due to eluates. The method wherein it is coated with a polymer having a low friction coefficient such as Teflon hardly exhibits sufficiently an easily-slippery property. The method of coating with a hydrophilic polymer exhibits an easily-slippery property being superior to these methods but there is a problem on its durability. For example, in fixation of polyvinylpyrrolidone with an isocyanate (Japanese Patent Laid-Open No.19,582/1984, U.S. Pat. No.4,100,309), the bonding between polyvinylpyrrolidone and the base material is not sufficient and an eluation occurs. Furthermore, in an improved method thereof wherein a hydrophilic polymer copolymerized with a reactive functional group and an isocyanate are used (Japanese Patent Laid-Open No.81,341/1984), these are not sufficiently solved. It is estimated that this is caused by a relatively easy hydrolysis of the bonding (amide bondings etc.). Moreover, in the fixation of polyethylene oxide with an isocyanate (Japanese Patent Laid-Open No.193,766/ 1983), there is similarly a problem on its durability.

As described above, there exists no method for providing an easily-slippery property exhibiting both characteristics, durability and safety. Namely, the purpose of the present invention is to offer a technology providing an excellent easily-slippery property which solves the problems of these conventional technologies.

DISCLOSURE OF THE INVENTION

The present invention is an easily-slippery medical material wherein the surface of a base material coated with the following component A is coated with the following component B Component A: A polymer having at least one reactive functional group selected from alkali metal alcoholate groups, amino group, alkali metal amide groups, carboxylic acid group, sulfonic acid group, magnesium halide groups and fluorinated boron complex groups.

Component B: A hydrophilic polymer having a reactive heterocyclic group being reactive with reactive functional groups in the component A. and the method of preparation thereof.

The best embodiment for Practicing the Invention

The present invention provides a medical material having excellent easily-slippery property and durability which conventional technologies have never been able to provide obtained by fixing a hydrophilic polymer on the surface of a base material through a covalent bonding and a method for preparation thereof.

The reactive functional group of the component A in the present invention is such a group that can react with the reactive heterocyclic group of the component B and those which are rich in anionic or cationic characteristics so as to open the heterocyclic ring are cited. As the practical example, alkali metal such as lithium, sodium and potassium alcoholate groups, primary and secondary amino groups, alkali metal amide groups, carboxylic acid group, sulfonic acid group, Grignard reagents such as magnesium halide group, fluorinated boron complex groups etc. can be cited. Among them, amino groups are preferably used as they are highly reactive.

As the polymer having such a reactive functional group, which is the component A, partially hydrolyzed products with alkali of polyvinyl acetate, hydrolyzed products with alkali of polymers having vinyl acetate as a copolymerizable component, alkali-treated products (alcoholates) of polymers having 2-hydroxyethyl (meth)acrylate as a copolymerizable component, hydrolyzed products (aminated products) of polyisocyanates, polymers having aminomethylstyrene as a copolymerizable component and amidated products thereof with alkali metals, polymers having styrene derivatives containing various amino groups such as 2-aminoethyl-4-vinyl-phynetylamine as a copolymerizable component and amidated products thereof with alkali metals, polymers having (meth)acrylic acid as a copolymerizable component, polymers having sulfonated styrene as a copolymerizable component, polymers having chloromethyl styrene as a copolymerizable component Grignardized with an active magnesium etc. are cited. As the practical examples, alkali-hydrolyzates of ethylene-vinyl acetate copolymers, vinyl chloride-vinyl acetate copolymers and methyl (meth)acrylate-vinyl acetate copolymers and acrylonitrile-vinyl acetate copolymers, alkali-treated products of methyl (meth)acrylate-2-hydroxyethyl (meth)acrylate copolymers, styrene-2-hydroxyethyl (meth)acrylate copolymers, acrylonitrile-2-hydroxyethyl (meth)acrylate copolymers, styrenehydroxystyrene copolymers and methyl (meth)acrylatehydroxystyrene copolymers, hydrolyzates (aminated products) of adducts of diphenylmethane-4,4'-diisocyanate or hexamethylenediisocyanate with trimethylolpropane and adducts of tolylene diisocyanate with trimethylolpropane, styrene-aminomethyl-styrene copolymers, methy (meth)acrylate-aminomethylstryene copolymers, styrene-2-aminoethyl-4-vinylphenetylamine copolymers, methyl (meth)-acrylate-2-aminoethyl-4-vinylphenylamine copolymers, vinylidene chloride-2-aminoethyl-4-vinylphenetylamine copolymers and acrylonitrile-2-aminoethyl-4-vinylphenetylamine copolymers and their amidated products with alkali metals (for example, lithium, sodium and potassium), acrylonitirle-(meth)acrylic acid copolymers, vinyl chloride-(meth)acrylic acid copolymers, vinylidene chloride-(meth)acrylic acid copolymers, methyl (meth)acrylate-(meth)acrylic acid copolymers, ethylene-(meth)acrylic acid copolymers, styrene-(meth)acrylic acid copolymers, and furthermore, Grignardized products of styrene-chloromethylstyrene copolymers, methyl (meth)acrylate-chloromethylstyrene copolymers, vinylidene chloride-chloromethylstyrene copolymers and acrylonitrilechloromethylstyrene copolymers are cited.

The content of said reactive functional groups in said component A is variably selected in accordance with the bonding force with the component B and the adhesive force and preferably selected in the range of 0.1–50 wt.%. The range of 1 - 30% is especially preferable. As the reactive heterocyclic group in the component B in the present invention, any heterocyclic group which can react with the reactive functional group of the coponent A can be used, but those ring structures which have high strain are preferable from the viewpoint of high reactivity. As the practical examples, ethylene oxide group, propylene oxide group, ethylene sulfide group, propylene sulfide group, cyclooxabutane group, Lactam and Lactone groups of a 3 or 4 membered ring, amino acid-N-carboxylic acid anhydride group (NCA), oxazolidine group, ethylene-imine group, propylene-imine group, cyclic ether groups such as dioxane, trioxane and tetraoxane cyclic azaether groups and thioether groups are cited. Ethylene oxide group is especially preferably selected as it is easily used.

The content of said reactive heterocyclic group in said component B is variably selected in accordance with the aimed characteristics, 0.01–50 wt.%, especially 0.1–30 wt.% is preferable in terms of the amount of the side chains containing the reactive heterocyclic group.

The hydrophilic polymers having said reactive heterocyclic groups, which are the component B, can be prepared by either of the following methods, namely, a method (1) wherein a monomer having a reactive heterocyclic group is copolymerized with a hydrophilic monomer and a method (2) wherein a compound having a reactive heterocyclic group is reacted with and thereby introduced in a hydrophilic polymer.

As the practical examples of the method (1), (meth)acrylamide-glycidyl (meth)acrylate copolymers, N-vinyl-2-pyrrolidone-glycidyl (meth)acrylate copolymers, monomethoxytriethylene glycol mono(meth)acrylate-glycidyl (meth)acrylate copolymers, monomethoxytetraethylene glycol mono(meth)acrylate-glycidyl (meth)acrylate copolymers, polyethylene glycol mono(meth)acrylate-glycidyl (meth)acrylate copolymers, 2-hydroxyethyl (meth)acrylateglycidyl (meth)acrylate copolymers, (meth)acrylamideglycidyl vinyl benzoate copolymers, N-vinylpyrrolidoneglycidyl vinyl benzoate copolymers, polyethylene glycol mono(meth)acrylate-glycidyl vinyl benzoate copolymers and 2-hydroxyethyl (meth)acrylate-glycidyl vinyl benzoate copolymers are representative ones, and any hydrophilic polymer obtained by copolymerizing a monomer providing hydrophilic nature such as (meth)acrylamide, N-vinylpyrrolidone, monomethoxytriethylene glycol mono(meth)acrylate, monomethyorytetraethylene glycol mono(meth)acrylate, polyethylene glycol mono(meth)acrylate having a molecular weight of 500–10,000, 2-hydroxyethyl (meth)acrylate, glyceryl (meth)acrylate, (meth)acrylic acid or its salts, 2-vinylpyridine and N-1,2,4-triazolyethylene with a reactive heterocyclic vinyl monomer of the following general formulas (I)–(V) can be used. The content of the reactive heterocyclic vinyl monomer is properly selected in accordance with the aimed characteristics and it is preferably in the range of 0.01–50 wt.% not to spoil the hydrophilic nature. Moreover, to impart physical strength to the hydrophilic polymer, it is preferably to copolymerize a hydrophobic monomer as the third component. In this case, the content of the third component is not specifically restricted as far as the hydrophilic nature is not spoiled, but the range of 0.01–50 wt.% is preferable. As the practical examples of the hydrophobic monomers which can be used, alkyl (meth)acrylates, vinyl chloride, vinylidene chloride, ethylene, (meth)acrylonitrile, propylene, vinyl acetate, styrene and styrene derivatives are cited. Moreover, as the molecular weight of these polymers, polymers having a molecular weight of 1,000–5,000,000 can be used and 100,000–2,000,000 is preferable.

As the practical examples of the method (2), compounds wherein a part of hydroxyl groups or amino groups contained in hydrophilic polymer such as cellulose, cellulose derivatives (methyl cellulose, ethyl cellulose,

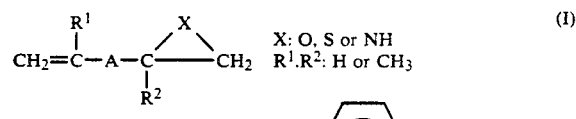

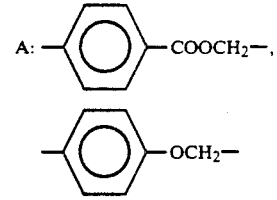

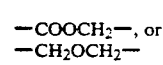

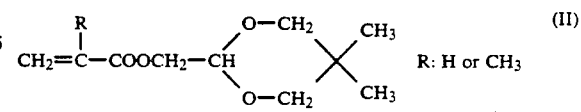

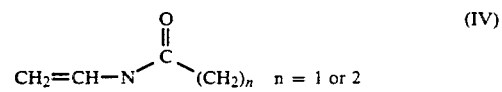

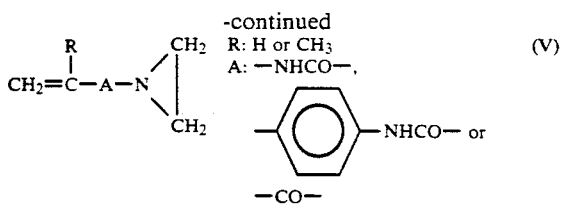

carboxymethylcellulose, cyanoethylcellulose, cellulose acetate, sodium salt of cellulose nitrate), amylose, amylopectin, alginic acid, heparin, pectin and water-soluble nylon are reacted with a compound of the following formula (VI) and a reactive heterocyclic ring is thereby introduced, are cited. In this case, the content of introduction of the reactive heterocyclic ring is not especially restricted as far as the aimed hydrophilic nature is not spoiled, but the range of 0.01-50 wt.% is preferable.

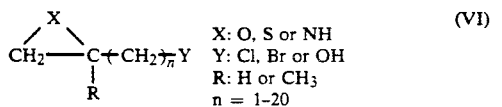

The hydrophilic coatings of the present invention have good easily-slippery property and durability caused by said constitution, but it is a desirable method to cure the component B after coating for improving the durability furthermore. Namely, it is possible to improve the physical strength without lowering the easily-slippery property by providing a three dimensional network structure. As the method for curing (crosslinking) like this, it is possible to apply generally various physicochemical means. For example, a method wherein said polymer is cured (crosslinked) by generating active radicals by using light, heat or radiation and moreover, a polymerizable polyfunctional monomer is therein additionally added. As a method for generating efficiently active radicals, it is preferable to use peroxides and azo compounds. It is especially preferable to use peroxides having a strong capability of drawing hydrogen. As the practical examples, acetyl peroxide, cumyl peroxide, propionyl peroxide, benzoyl peroxide, tert-butyl performate, potassium persulfate etc. are cited. The loading of these compounds to the component B is properly selected in accordance with the aimed characteristics, but the range of 0.001-20 wt.% is preferable. Moreover, as the practical examples of polymerizable polyfunctional monomer which can be incorporated to cure (crosslink) furthermore efficiently, divinylbenzene, ethylene glycol di(meth)acrylate, trimethylolpropane or pentaerythritol di-, tri- or tetra- (meth)acrylate, diethylene glycol or polyethylene glycol di(meth)acrylate can be cited. The loading of these compounds to the component B is properly selected in accordance with the aimed characteristics, but the range of 0.1-30 wt.% is preferably selected.

Next, the method for forming the medical materials having easily-slippery property of the present invention will be explained in more detail.

The base material is variably selected in accordance with the purpose of use and various plastics, inorganic materials and metallic materials are suitably used. As the practical examples, polyvinyl chloride, polyethylene, polypropylene, polystyrene, polyurethane, polyurea, polymethyl methacrylate, nylon, polyester, poly- acrylonitrile, metallic wires coated therewith, stainless steel, elastic metals, ceramics and wood are cited.

As the methods for coating the surfaces of these base materials with the component A, it is preferable that dipping or spin coating is carried out by using a solution wherein a specified amount of the component A is dissolved in a proper good solvent and then drying is done. As the solvents to be used, alcohols, aromatic hydrocarbons, linear or cyclic hydrocarbons, halogenated hydrocarbons, ketones and amides are preferable. The concentration of the component A in the solution can be properly selected in accordance with the aimed thickness of coating, but the range of 0.01-50 wt.% is preferably used. The range of 1-10 wt.% is especially preferable.

Then, the surface of a base material coated with the component A is coated with the component B. The method of coating is the same as the method of coating for the component A, namely, dipping or spin coating is carried out by using a solution wherein a specified amount of the component B is dissolved in a proper good solvent and then drying is done. As the solvents, besides said solvent, water can be also used. The concentration of the component B in the solution can be properly selected in accordance with the aimed thickness of coating, but the range of 0.01-50 wt.% is preferably used. The range of 1-10 wt.% is especially preferable. When a curing (crosslinking) agent such as peroxides, azo compounds and polymerizable polyfunctional monomers is used, it is preferable that the specified amount thereof is added in this solution.

After coatings with the component A and the component B, a reaction of the component A with the component B is carried out by carrying out successively by a heat treatment. The heating condition, the time and the temperature are properly selected in accordance with the nature of the reaction and existence of a curing (crosslinking) reaction and one of the preferable range is 30°-200° C. and 1 min-24 hr. It is also a preferable method to carry out the reaction in various inert gases for suppressing side reactions. "Examples"

The present invention will be explained in more detail heretobelow by examples, but is not restricted thereby.

EXAMPLE 1

As a component B, acrylamide-glycidyl methacrylate copolymer having a molecular weight of about 200,000 was obtained by polymerizing 9.0 g of acrylamide and 1.0 g of glycidyl methacrylate in dimethyl sulfoxide (DMSO) by using AIBN (azobisisobutyronitrile) as an initiator.

A wire having a diameter of 2 mm prepared by coating a stainless wire with a polyurethane was immersed in a 2% polyisocyanate (manufactured by Nippon Polyurethane Industries Co., Ltd., The name of the product: C-L, TDI/TMP adduct) solution in methyl ethyl ketone (MEK) for 1 min and the coated wire was dried at 50° C. for 1 hr. Then, this was immersed in 0.1 N sodium hydroxide ag. solution at 40° C. for 1 hr to hydrolyze it and to form amino groups.

Then, this wire was immersed in a 5% acrylamide-glycidyl methacrylate copolymer aq. solution for 5 sec and pulled up and the reaction was carried out at 100° C. for 5 hr.

The obtained wire coated with the hydrophilic coating exhibited excellent easily-slippery property when it was wetted with a physiological saline or water and also exhibited excellent easily-slippery property after 1 hr boiling, which meant excellent durability.

EXAMPLE 2

As a component A, methyl methacrylate-2-hydroxyethyl methacrylate copolymer having a molecular weight of about 100,000 was obtained by polymerizing 8.0 g of methyl methacrylate and 2.0 g of 2-hydroxyethyl methacrylate in isopropyl alcohol by using AIBN (azobisisobutyronitrile) as an initiator.

Then, the same wire as that of Example 1 was immersed in a 3% solution of this polymer in dioxane for 1 min and dried at 50° C. for 1 hr. Furthermore, this was immersed in 1 N sodium hydroxide aqueous solution to form sodium alcoholate.

Then, as a component B, the same compound as that of Example 1 was used and was reacted by means of the same method.

The obtained wire coated with the hydrophilic coating exhibited excellent easily-slippery property when it was wetted with a physiological saline or water and also exhibited excellent easily-slippery property after 1 hr boiling, which meant excellent durability.

EXAMPLE 3

As a component B, N-vinylpyrrolidone-glycidyl acrylate copolymer having a molecular weight of about 300,000 was obtained by polymerizing 9.0 g of N-vinylpyrrolidone and 1.0 g of glycidyl acrylate by using V-65 (azobisvaleronitrile) as an initiator.

The same treatment as that of Example 1 was performed by using the same materials as those of Example 1 as both a component A and a base material (wire).

Then, this wire was immersed in 3% solution of the previously synthesized N-vinylpyrrolidone-glycidyl acrylate copolymer in chloroform for 5 sec, pulled out therefrom, dried and reacted at 100° C. for 5 hr.

The obtained wire coated with the hydrophilic coating exhibited excellent easily-slippery property when it was wetted with a physiological saline or water and also exhibited excellent easily-slippery property after 1 hr boiling, which meant excellent durability.

EXAMPLE 4

A hydrophilic coating was formed by the same method as that of Example 3 except using N-vinylpyrrolidone-vinyl acetate-glycidyl acrylate copolymer having a molecular weight of about 500,000 obtained by polymerizing 7.0 g of N-vinylpyrrolidone, 2.0 g vinyl acetate and 1.0 g of glycidyl acrylate in ethyl alcohol by using V-65 (azobisvaleronitrile) as an initiator as a component B.

The obtained wire exhibited excellent easily-slippery property when it was wetted with a physiological saline or water and it was found that it exhibited excellent easily-slippery property after 1 hr boiling and had excellent durability.

EXAMPLE 5

A hydrophilic coating was formed by the same method as that of Example 3 except using N-vinylpyrrolidone-ethyl acrylate-lycidyl acrylate copolymer having a molecular weight of about 600,000 obtained by polymerizing 8.0 g of N-vinylpyrrolidone, 1.5 g of ethyl acrylate and 0.5 g of glycidyl acrylate in isopropyl alcohol by using V-65 as an initiator as a component B. In this Example, a procedure wherein after heat-reaction for 1 hr, it was immersed in water for 1 min and then heat-reaction was performed again, was furthermore added.

The obtained wire exhibited excellent easily-slippery property when it was wetted with a physiological saline or water and it was found that it exhibited excellent easily-slippery property after 1 hr boiling and had excellent durability.

EXAMPLE 6

As a component B, monomethoxytetraethylene glycol monomethacrylate-glycidyl vinyl benzoate copolymer having a molecular weight of about 1000,000 was obtained by polymerizing 9.5 g of monomethoxytetraethylene glycol monomethacrylate and 0.5 g of glycidyl vinyl benzoate in tetrahydrofuran by using AIBN (azobisisobutyronitrile) as an initiator.

The same component A and base material (wire) as those of Example 2 were used and treated with the same method as that of Example 2. Then, this wire was immersed in 5% previously synthesized monomethoxytetraethylene glycol monomethacrylate-glycidyl vinyl benzoate copolymer solution in dimethylacetamide for 5 sec, pulled up, dried and reacted at 100° C. for 5 hr.

The obtained wire exhibited excellent easily-slippery property when it was wetted with a physiological saline or water and it was found that it exhibited especially excellent easily-slippery property after 1 hr boiling and had excellent durability.

EXAMPLE 7

A hydrophilic coating was formed by the same method as that of Example 3 except adding 1% of benzoyl peroxide (based on the polymer) to N-vinylpyrrolidone-glycidyl acrylate copolymer and carrying out the reaction under reaction conditions which were at 120° C., for 5 hr under nitrogen atmosphere.

The obtained wire exhibited excellent easily-slippery property when it was wetted with a physiological saline or water and it was found that it exhibited especially excellent easily-slippery property after 1 hr boiling and had excellent durability.

EXAMPLE 8

A hydrophilic coating was formed by the same method as that of Example 4 except adding 1% of benzoyl peroxide (based on the polymer) and 5% of tetraethylene glycol dimethacrylate (based on the polymer) to N-vinylpyrrolidone-vinyl acetate-glycidyl acrylate copolymer used in Example 4 and carrying out the reaction under reaction conditions which were at 120° C. for 5 hr under nitrogen atmosphere.

The obtained wire exhibited excellent easily-slippery property when it was wetted with a physiological saline or water and it was found that it exhibited especially excellent easily-slippery property after 1 hr boiling and had excellent durability.

COMPARATIVE EXAMPLE 1

The same polyurethane-coated wire as that of Example was immersed in 2% polyisocyanate (manufactured by Nippon Polyurethane Industries Co., Ltd., The name of the product: C-L, TDI/TMP adduct) solution in methyl ethyl ketone (MEK) for 1 min and dried at 50° C. for 1 hr. Then, this was immersed in 4% polyvinylpyrrolidone (manufactured by Polysciences, Inc., the molecular weight was 360,000) solution in chloroform for 5 sec, pulled up, dried and then reached at 80° C. for 5 hr. When the obtained wire was wetted with a physiological saline or water, it exhibited excellent easily-slippery property at the beginning, but after a repeated test of several times or boiling for several min, it exhibited no easily-slippery property at all and as the result, it was found that the durability was poor.

Comparative Example 2

A sample was prepared by the same method as that of Comparative Example 1 except using polyethylene glycol (the molecular weight was 6,000) as a hydrophilic polymer. The obtained wire did not exhibit good easily-slippery property when it was wetted with a physiological saline or water and it became not to exhibit easily-slippery property at all after a repeated test of several times or boiling for several min and as the result, it was found the durability was poor.

The results of evaluation in Examples 1-8 and Comparative Example 1 and 2 are shown in Table 1.

TABLE 1

| No. | Evaluation Easily-slippery property | |
|---|---|---|
| | Initial | After boiling for 1 hr |
| Example | | |
| 1 | ○ | ○ |
| 2 | ○ | ○ |
| 3 | ⊙ | ○ |
| 4 | ⊙ | ⊙ |
| 5 | ⊙ | ⊙ |
| 6 | ⊙ | ○ |
| 7 | ⊙ | ⊙ |
| 8 | ⊙ | ⊙ |
| Comparative example | | |
| 1 | ⊙ | x |
| 2 | △ | x |

⊙: Especially good, ○: Good, △: Average, x: poor

Possibility of Industrial Application

The easily-slippery material of the present invention can be widely applicable in a variety of fields. Above all, as this material has both excellent easily-slippery property and durability (safety), it is applicable for medical materials such as catheters, guide wires, endoscopes, contact lenses and condom. Moreover, it has excellent biocompatibility as it has a hydrophilic nature and when it is applied for medical materials, it is expected that besides said characteristics, such excellent characteristics as high anti-thrombus characteristics can be obtained.

We claim:

1. A slippery medical material wherein the surface of a base material coated with a component A is followed by a coating with a component B, wherein said component A comprises a polymer having at least one reactive functional group selected from the group consisting of an alkali metal alcoholate group, amino group, an alkali metal amide group, a carboxylic acid group, a sulfonic acid group, a magnesium halide group and a fluorinated boron complex group; and said component B comprises a hydrophilic polymer having a reactive heterocyclic group being reactive with the reactive functional group in the component A.

2. An easily-slippery medical material as described in claim 1 wherein the component A is a polymer having amino groups.

3. An easily-slippery medical material as described in claim 1 wherein the content of said reactive functional groups in the component A is 0.1-50 wt.%.

4. An easily-slippery medical material as described in claim 1 wherein the reactive heterocyclic group in the component B is at least one selected from the groups consisting of ethylene oxide group, propylene oxide group, ethylene sulfide group, propylene sulfide group, cyclooxabutane group, lactam and lactone groups of a 3 or 4 membered ring, amino acid-N-carboxylic acid anhydride group, oxazolidine group, ethylene-imine group, propylene-imine group, cyclic ether groups, cyclic azaether groups and cyclic thioether groups.

5. An easily-slippery medical material as described in claim 1 wherein the reactive heterocyclic group in the component B is ethylene oxide group.

6. An easily-slippery medical material as described in claim 1 wherein the content of the reactive heterocyclic group in the component B is 0.01-50 wt.%.

7. An easily-slippery medical material as described in claim 1 wherein the component B is a copolymer consisting of a monomer having a reactive heterocyclic group and a hydrophilic monomer.

8. An easily-slippery medical material as described in claim 7 wherein the hydrophilic monomer is at least one selected from the group consisting of (meth)acrylamide, N-vinylpyrrolidone and monomethoxytriethylene glycol mono(meth)acrylate.

9. A method of preparing a slippery medical material comprising the steps of (1) applying to the surface of a base material a coating of component A, and thereafter (2) applying thereover a coating of component B, wherein said component A comprises a polymer having at least one reactive functional group selected from the group consisting of an alkali metal alcoholate group, an amino group, an alkali metal amide group, a carboxylic acid group, a sulfonic acid group, a magnesium halide group and a fluorinated boron complex group; and said component B comprises a hydrophilic polymer having a reactive heterocyclic group being reactive with the reactive functional group in the component A.

10. A method for preparation of an easily-slippery medical material as described in claim 9 wherein the component A is a polymer having at least one reactive functional group selected among alkali metal alcoholate groups, amino groups, alkali metal amide groups, carboxylic acid group, sulfonic acid group, magnesium halide groups and fluorinated boron complex groups.

11. A method for preparation of an easily-slippery medical material as described in claim 9 wherein the component A is a polymer having amino groups.

12. A method for preparation of an easily slippery medical material as described in claim 9 wherein the content of said reactive functional groups in the component A is 0.1-50 wt.%.

13. A method for preparation of an easily-slippery medical material as described in claim 9 wherein the reactive heterocyclic group in the component B is at least one selected from the groups consisting of ethylene oxide group, propylene oxide group, ethylene sulfide group, propylene sulfide group, cyclooxabutane group, lactam and lactone groups of 3 or 4 membered ring, amino acid-N-carboxylic acid anhydride group, oxazolidine group, ethylene-imine group, propylene-imine group, cyclic ether groups, cyclic azaether groups and cyclic thioether groups.

14. A method for preparation of an easily-slippery medical material as described in claim 9 wherein the reactive heterocyclic group in the component B is ethylene oxide group.

15. A method for preparation of an easily-slippery medical material s described in claim 9 wherein the component B is a copolymer consisting of a monomer having a reactive heterocyclic group and a hydrophilic monomer.

16. A method for preparation of an easily-slippery medical material as described in claim 15 wherein the hydrophilic monomer is at least one selected from the group consisting of (meth)acrylamide, N-vinyl-pyrrolidone and monomethoxy-triethylene glycol mono(meth)acrylate.

17. A method for preparation of an easily-slippery medical material as described in claim 9 characterized by using a peroxide, an azo compound or a polymerizable polyfunctional monomer as a crosslinking agent.

18. A method for preparation of an easily-slippery medical material as described in claim 9 characterized by carrying out a heat-treatment after coating with the component A and the Component B.

19. A method for preparation of an easily-slippery medical material as described in claim 18 characterized by carrying out a heat-treatment at 30°–200° C. for 1 min–24 hr.

20. A method for preparation of an easily-slippery medical material as described in claim 18 characterized by carrying out a heat-treatment in an inert gas.

* * * * *